United States Patent [19]

Ishihara et al.

[11] Patent Number: 6,110,123
[45] Date of Patent: Aug. 29, 2000

[54] REGION-OF-INTEREST SETTING APPARATUS FOR RESPIRATION MONITORING AND A RESPIRATION MONITORING SYSTEM

[75] Inventors: Ken Ishihara, Takarazuka; Yoshio Miyake, Kawasaki; Hiroaki Nakai; Mutsumi Watanabe, both of Kobe; Keisuke Takada, Kawasaki, all of Japan

[73] Assignee: Toshiba Engineering Corp., Kanagawa-ken, Japan

[21] Appl. No.: 09/196,197

[22] Filed: Nov. 20, 1998

[30] Foreign Application Priority Data

Nov. 21, 1997 [JP] Japan .................................. 9-321324
Nov. 13, 1998 [JP] Japan .................................. 10-324129

[51] Int. Cl.⁷ .................................................. A61B 5/08
[52] U.S. Cl. .................................... 600/534; 600/529
[58] Field of Search ................................ 600/534, 529, 600/300

[56] References Cited

U.S. PATENT DOCUMENTS

| | | | |
|---|---|---|---|
| 4,975,960 | 12/1990 | Petajan . | |
| 5,363,844 | 11/1994 | Riederer et al. | 600/413 |
| 5,577,502 | 11/1996 | Darrow et al. | 600/426 |
| 5,689,241 | 11/1997 | Clarke, Sr. et al. | 340/575 |
| 5,704,367 | 1/1998 | Ishikawa et al. | 600/473 |

FOREIGN PATENT DOCUMENTS 8-257015  10/1996  Japan .

OTHER PUBLICATIONS

Duffy et al. "Optical non–contact measurement of abdominal volume change during anaesthesia", IEE Colloquium on Optical Techniques and Biomedical Applications, Jun. 14, 1991, pp. 8/1–8/4.

Nakajima et al. "Evaluation of Body Motion by Optical Flow Analysis", Japanese Journal of Applied Physics, vol. 36, No. 5A, May 1997, pp. 2929–2937.

European Search Report Dated Mar. 9, 1999.

Ishihara et. al., "Automatic Measurements of the Number of Respirations Under Complete Non–restrictions by a Visual Sensing System", 16th Bio–Mechanism Society Conference, Nov. 25, 1995, pp. 279–282.

*Primary Examiner*—Cary O'Connor
*Assistant Examiner*—Navin Natnithithadha
*Attorney, Agent, or Firm*—McGinn & Gibb, P.C.

[57] ABSTRACT

A region-of-interest (ROI) setting apparatus for respiration monitoring and a respiration monitoring system capable of setting an ROI in an automatic manner. Absolute values of subtractions between every successive two of a plurality of frame images photographed by a CCD camera 2 for a period of time equal to half a respiration period are calculated, then summed and stored. Based on the change information thus calculated and stored, the position and size of each changed region is calculated. Provisional regions are set from the changed regions successively from the greatest to the smallest one thereof. In each of these provisional regions, it is determined whether a gray level histogram indicative of distribution of the number of pixels for respective gray level values includes a twin peak characteristic having twin peaks each equal to or higher than a predetermined value, and whether the area of the corresponding changed region is equal to or greater than a predetermined value. One of the provisional regions that satisfies these conditions is set as an ROI.

20 Claims, 7 Drawing Sheets

INFORMATION OF CHANGE IN IMAGES OBTAINED BY SUBTRACTING & SUMMING CIRCUIT

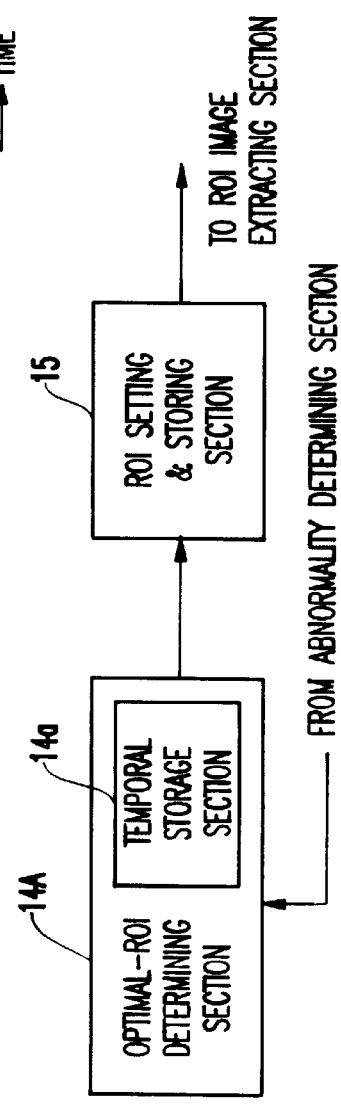
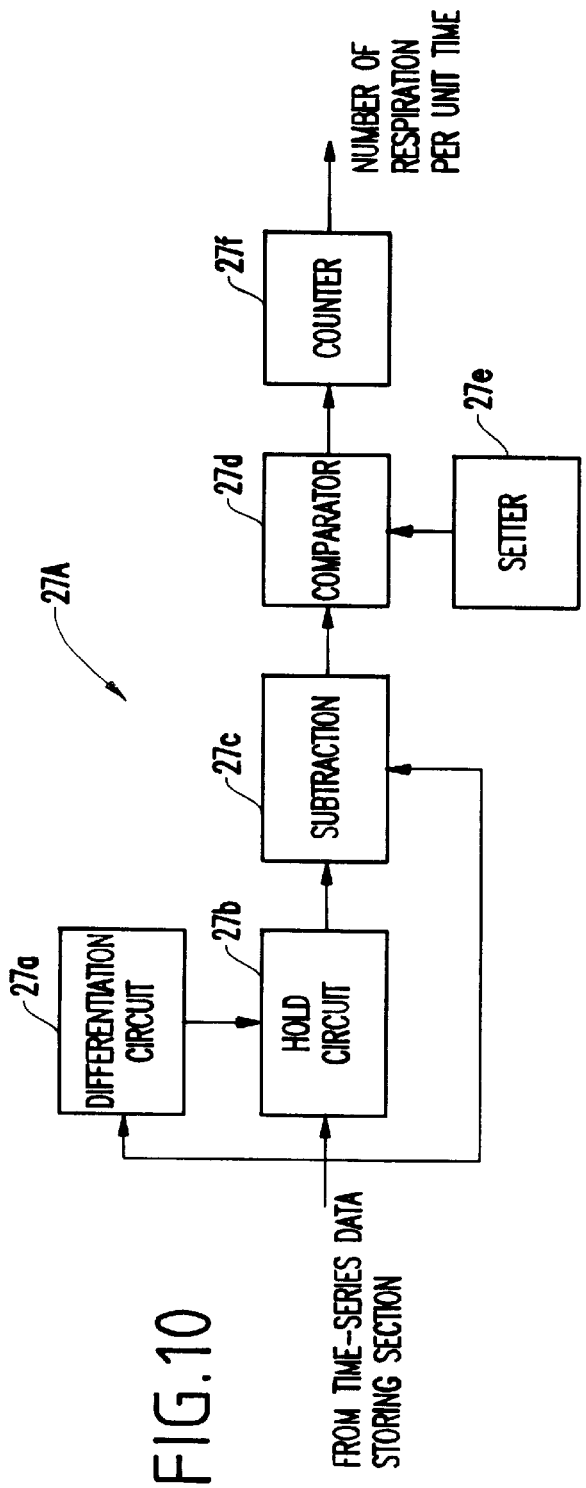
FIG. 8
FIG. 9
FIG. 10

REGION-OF-INTEREST SETTING APPARATUS FOR RESPIRATION MONITORING AND A RESPIRATION MONITORING SYSTEM

BACKGROUND OF THE INVENTION

1. Field of the Invention

The present invention relates to a respiration monitoring system which is capable of continuously monitoring the respiratory state of a person such as a patient through visual sensing in a non-restrictive manner. It also relates to an apparatus for setting a region of interest for respiration monitoring.

2. Description of the Related Art

In recent years, the number of persons of advanced age has rapidly increased, and thus the number of staff members caring for bed-ridden elderly persons has likewise increased, thereby increasing personnel costs therefore and medical care expenditures. Such increased costs have become an object of great public concern.

Accordingly, it has hitherto been known that respiration monitoring systems have been developed which are capable of continuously monitoring the respiratory state of a bed-ridden aged person and the like through visual sensing in a non-restrictive manner.

FIG. 13 diagrammatically shows a typical example of a conventional respiration monitoring system entitled "Automatic Measurements of the Number of Respirations under Complete Non-restrictions by a Visual Sensing System" that was reported in the proceeding of the 16th Bio-Mechanism Society Conference held on Nov. 25, 1995 by the Bio-Mechanism Society on pages 279 through 282.

This respiration monitoring system includes a CCD camera 2 for imaging or photographing the chest of a patient 1 as an object to be imaged who is lying on a bed, an image processor 3 connected to an output of the CCD camera 2 for successively extracting an inter-image difference or subtraction (i.e., subtraction between every two successive images) of continuous motion pictures at a constant period of time and performing predetermined image processing so as to obtain or calculate a changed component to thereby measure the number of respirations per unit time, a monitor 4 connected to an output of the image processor 3 for displaying a visual indication of the detected data including the measured number of respirations per unit time, the state of respiration and/or displaying an abnormal state in the case of an abnormality taking place, and a setting input section 5 through which an operator can input various settings such as a processing region in the form of a region of interest (hereinafter simply referred to as ROI) of the image processor 3, an interval of subtraction ($\alpha$) in the image processing, etc.

FIG. 14 is a flow chart showing an operation (i.e., respiration counting operation) of the above-mentioned conventional respiration monitoring system.

Now, the operation of the conventional respiration monitoring system will be described in detail while referring to the flow chart of FIG. 14.

First in step S1, the image processor 3 successively receives image data from the CCD camera 2, and in step S2, it performs signed (+, −) subtraction of pixels between every two adjacent images that are spaced a predetermined distance from each other in the form of a frame interval ($\alpha$). Subsequently, in step S3, the image processor 3 performs surface integration within a ROI. Specifically, the surface integration is carried out as follows. The image data extracted are subjected to signed subtraction (i.e., subtraction with a plus or minus sign) to provide binarized images, from which an area of variations for each image is calculated. Each area thus obtained is then surface integrated in terms of brightness to provide a signed changing speed or rate of each changed portion. Then, in step S4, the signed changing speed thus obtained is processed in a time-series manner each time the CCD camera 2 takes one frame, on the basis of the result of which respiration counting is carried out in step S5.

In this manner, the conventional respiration monitoring system can monitor the state of respiration through visual sensing in a non-restrictive and continuous manner.

With the above-mentioned respiration monitoring system, however, a watch man or supervisor who also acts as an operator has to manually input the setting of a specific region of interest (ROI) among the pictures or images photographed by the CCD camera 2, for which region image processing is to be performed for measuring or counting the number of respirations per unit time, while watching the monitor 4, as referred to above.

Thus, with the conventional respiration monitoring system in which the ROI setting is input manually by an operator, if, for example, a person such as a patient to be monitored or photographed has moved to displace the ROI, it becomes unable, if not impossible to measure or count the number of respirations per unit time in an accurate manner or the respiration measurement or counting becomes impossible when such a situation is left unattended. As a result, it will be impossible to automatically measure the respiration for a long period of time. On the other hand, if the deviation or displacement of the ROI (i.e., movement of the person) is monitored by the watch man in order to make it possible to effect a long-term accurate respiration counting, it becomes impossible to achieve the intended purpose of reducing the personnel expense and the amount of labor required through automatic respiration counting.

Moreover, in this case, a change in the value of surface integration becomes small depending upon the position of setting of the ROI, so the accuracy of respiration counting can be reduced due to influences of noise or the like, or it will be difficult to recognize inhalation and exhalation of the person on a monitor.

Furthermore, with the conventional respiration monitoring system, the frame interval $\alpha$ for subtraction is also set and input by the operator, so similar to the setting of the ROI, it is difficult to perform long-term respiration counting. In addition, the frame interval $\alpha$ is input by the operator based on his or her experience, so the accuracy of respiration counting depends on the setting for $\alpha$ and sometimes decreases due to an inappropriate setting, with the result that recognition of inhalation and exhalation on the monitor becomes difficult.

Further, the conventional respiration monitoring system calculates the speed or rate of change in the darkness or gray level within the ROI using an inter-image subtraction with a plus or minus sign, and hence, if an increase and a decrease of brightness within the ROI are equal in their areas to each other, it is determined that there is no change in the speed.

SUMMARY OF THE INVENTION

The present invention is intended to obviate the above-mentioned problems encountered with the conventional respiration monitoring system, and has as its object to provide a novel and improved apparatus for setting a region of interest for respiration monitoring and a respiration monitoring system which are capable of performing accurate respiration counting for an extended period of time in an automatic manner, maintaining a high degree of respiration counting accuracy, and carrying out the recognition of inhalation and exhalation of a person on a monitor in an easy way.

In order to obviate the above problems, according to a first aspect of the present invention, there is provided a region-of-interest setting apparatus for respiration monitoring comprising:

photographing means (a CCD camera 2) for photographing an object to be monitored;

provisional-region setting means for extracting changed portions between successive images taken by said photographing means and setting an optimal one of the thus extracted changed portions as a provisional region;

determining means (an optimal-ROI determining section 14) for determining whether said provisional region set by said provisional-region setting means can be adopted as a changed region for respiration counting; and region-of-interest setting means (an ROI setting and storing section 15) for setting said provisional region as a region of interest for respiration counting when said determining means determines that said provisional region can be adopted as a changed region for respiration counting.

With the above arrangement, it is possible to set the region of interest in an automatic manner.

In a preferred form of the first aspect of the invention, said provisional-region setting means comprises:

subtracted-image storing means (e.g., an original image memory 11 and a subtraction and summation circuit 12) for calculating absolute values of subtractions between every successive two of a plurality of frame images taken during at least half a respiration period, and for summing up and storing the absolute values of subtractions of the images thus obtained for every predetermined frames; and region-of-interest candidate setting means for calculating the position and size of each of said changed regions based on brightness information of each subtracted image stored in said subtracted-image storing means and setting at least the greatest among the changed regions as a provisional region.

With the above arrangement, for a candidate of the region of interest, a single region can be selected in which there can be seen changes over the largest area, and hence it is possible to list up as an ROI candidate a region for which a sufficient respiration measuring or counting accuracy can be ensured against noise.

In another preferred form of the first aspect of the invention, said provisional-region setting means comprises:

subtracted-image storing means for calculating absolute values of subtractions between every successive two of a plurality of frame images taken during at least half a respiration period, and for summing up and storing the absolute values of subtractions of the images thus obtained for every predetermined frames; and region-of-interest candidate setting means (e.g., a candidate-region extracting section 13) for calculating the position and size of each of said changed regions based on brightness (change) information of each subtracted image stored in said subtracted-image storing means and setting an optimal one of the changed regions successively from the greatest to the smallest thereof as a provisional region.

With the above arrangement, in cases where a large region is not used for setting a region of interest, the next candidate can be fetched or retrieved, thus obviating the necessity of again performing a provisional region setting operation. This leads to an enhancement in processing.

In a further preferred form of the first aspect of the invention, said determining means determines whether in said provisional region set by said provisional-region setting means, a gray level histogram indicative of distribution of the number of pixels for respective gray level values includes a twin peak characteristic having twin peaks each equal to or higher than a predetermined value. In one embodiment, the determining means comprises an optimal-ROI determining section 14, and the predetermined value is set in such a manner that peaks of the twin-peak characteristic can be detected against noise.

According to the above features, on the condition that the gray level histogram has a vertical difference (i.e., difference between the highest and lowest points) not less than a predetermined value, it is possible to select, among the ROI candidates, an optimal region of interest in which a sufficient difference in contrast can be detected to provide a satisfactory accuracy in optical measurements. In this case, since the twin peak characteristic is a required condition, reliability in maintaining measuring accuracy can be further enhanced.

In a yet further preferred form of the first aspect of the invention, said determining means (an optimal-ROI determining section 14) determines whether the area of said changed region is equal to or greater than a predetermined value.

According to this feature, it is possible not only to select an optimal region of interest for which sufficient measuring accuracy can be obtained against noise, but also to easily observe or recognize variations in exhalation and inhalation of the object such as a patient on a monitor for example.

In a still further preferred form of the first aspect of the invention, when said determining means (an optimal-ROI determining section 14) determines that said provisional region set by said provisional region setting means can not be adopted as a changed region for respiration counting, said provisional region setting means again performs the setting of a provisional region.

According to this feature, the process of setting a region of interest is carried out repeatedly until an optimal region of interest is set, thereby increasing reliability in the ROI setting.

In a further preferred form of the first aspect of the invention, the region-of-interest setting apparatus for respiration monitoring further comprises region-of-interest setting starting-condition determining means (e.g., an object detecting section 40) for detecting, as a condition for starting the setting of a region of interest, whether the object to be monitored has come into a field of view of said photographing means.

With this arrangement, even if the object in the form of a person to be monitored has left a bed, when the person thereafter returns to the bed, a region of interest is automatically set once again, so respiration monitoring can be resumed in an automatic manner.

In accordance with a second aspect of the present invention, there is provided a respiration monitoring system comprising:

photographing means (a CCD camera 2) for photographing an object to be monitored;

setting means for setting a region of interest for respiration counting in images taken by a photographing means;

change detecting means (e.g., an ROI image extracting section 21, a previous-frame memory 22, a frame-memory selecting section 23, an inter-image subtraction section 24 and a surface integration section 25) for calculating absolute values of subtractions between successive two images taken by said photographing means in the region of interest set by said setting means and for summing up the absolute values of subtractions for every predetermined number of frames;

counting means (e.g., a time-series data storing section and a respiration calculating section) for counting the number of respirations per unit time based on a trend of time-series changes obtained by said change detecting means.

With the above arrangement, the absolute values of subtractions between two successive images are summed up for every predetermined number of frames, so that even if the brightness in the region of interest changes with the area of increasing brightness equal to the area of decreasing brightness, such changes can be detected correctly, thus preventing errors in measurements which would otherwise result from non-detection of the changes as in the prior art.

In a preferred form of the second aspect of the invention, the respiration monitoring system further comprises condition determining means for determining, based on a frequency analysis of a trend of time-series data, whether the state of respiration is normal.

With this arrangement, a discrimination can be clearly made as to whether the trend of time-series data is generated based on noise and the like, or on normal respiration.

In another preferred form of the second aspect of the invention, the respiration monitoring system further comprises existence determining means for determining whether the object to be monitored has gone out of a predetermined range of photographing.

With the above arrangement, it is determined whether the object such as, for example, a patient to be monitored goes out of a range to be monitored or photographed, for example, in such a case where the patient gets away from a bed for lingering or some other reason, or falls down from bed. This serves to improve reliability in respiration monitoring.

In a further preferred form of the second aspect of the invention, the respiration counting means counts the number of respirations per unit time by measuring the number of peaks in a change of a trend in the time series data, and wherein a threshold is used which is variably set for each peak for counting thereof.

According to this feature, the number of respirations per unit time can be counted reliably. That is, the magnitude of each peak occurring in the trend of the time-series data generally changes, and in such a case, if the number of peaks is counted with a constant threshold, there will be a problem that peaks smaller than the threshold can not be counted. To cope with this problem, the threshold can be set dependent on the magnitude of each peak, so that the number of peaks can be counted correctly irrespective of variations in the peak magnitude.

In a still further preferred form of the second aspect of the invention, the respiration monitoring system further comprises frame-interval setting means (a frame-interval setting section 28) for setting the predetermined number based on the summed value calculated by the change detecting means or the number of respirations per unit time counted by the counting means in such a manner as to emphasize changes in gray levels.

With the above arrangement, measuring accuracy can be improved, and observation of changes on a monitor for example can be effected with ease.

In a yet further preferred form of the second aspect of the invention, the means for setting a region of interest for respiration counting in images taken by a photographing means comprises the region-of-interest setting means (an ROI setting section 10) of the region-of-interest setting apparatus for respiration monitoring according to the first aspect of the present invention.

With the above arrangement, the entire process of respiration monitoring including the setting of a region of interest can be automated so that respiration of the object such as a patient can be monitored for an extended period of time without requiring any watch man.

In a further preferred form of the second aspect of the invention, the provisional region setting means and/or the determining means operate(s) during respiration counting.

According to this feature, for example, in cases where the ROI needs to be set again during respiration counting, such a new setting can be readily made immediately, thus avoiding interruption of respiration monitoring for a long period of time.

The above and other objects, features and advantages of the present invention will become apparent from the following detailed description of the invention taken in conjunction with the accompanying drawings.

BRIEF DESCRIPTION OF THE DRAWINGS

FIG. 8 is a time chart showing the respiration speed or rate in terms of the absolute value of subtraction;

FIG. 9 is a block diagram showing an optimal-ROI determining section of a respiration monitoring system in accordance with a second embodiment of the present invention;

FIG. 10 is a block diagram showing a respiration rate calculating section of a respiration monitoring system in accordance with a third embodiment of the present invention;

DESCRIPTION OF THE PREFERRED EMBODIMENTS

Now, preferred embodiments of the present invention will be described in detail while referring to the accompanying drawings.

Embodiment 1

Figure 1:
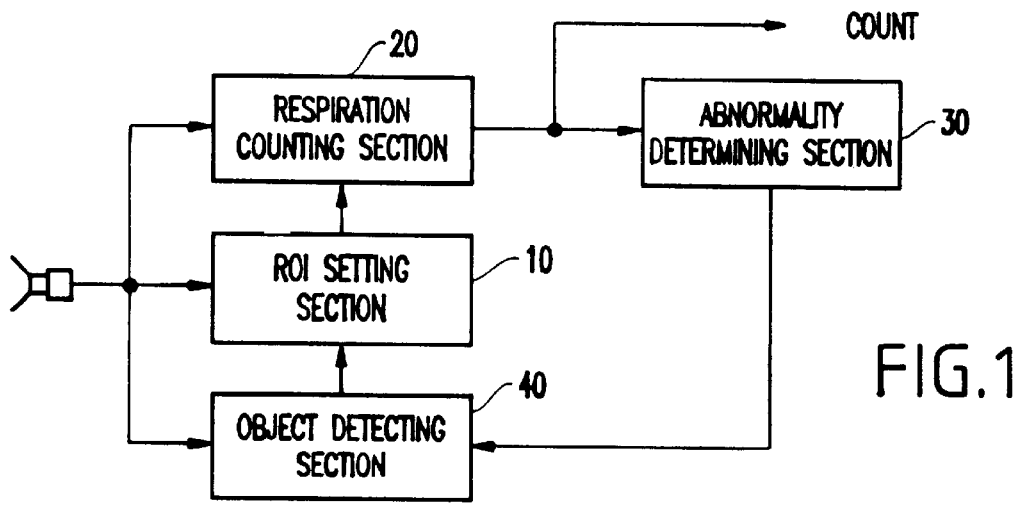
FIG. 1 is a block diagram showing the overall arrangement of a respiration monitoring system in accordance with a first embodiment of the present invention.

FIG. 1 schematically shows in block form the overall arrangement of a respiration monitoring system constructed in accordance with the principles of the present invention.

The respiration monitoring system comprises a CCD camera 2 for sensing or photographing the breast or thereabouts of a target object such as an aged person, patient, etc., who is being cared, for a region-of-interest (ROI) setting section 10 connected to an output of the CCD camera 2 for setting a region of interest, a respiration counting section 20 connected to an output of the ROI setting section 10 and the output of the CCD camera 2 for measuring or counting the number of respirations per unit time in the region of interest (ROI) which is set by the ROI setting section 10, an abnormality determining section 30 connected to an output of the respiration counting section 20 for measuring whether the number of respirations per unit time measured is normal or abnormal, and an object detecting section 40 connected to an output of the abnormality determining section 30 and the output of the CCD camera 2 for detecting the target object to be monitored or photographed.

The object detecting section 40 detects the target object coming into the screen or view of the CCD camera 2 upon setting of the ROI by continuously detecting a large displacement of the target object on a picture image for a predetermined period of time, and generates a detection or output signal which acts as a trigger to actuate the ROI setting section 10. Also, when the target object temporarily gets away from a bed or the like, the abnormality determining section 30 determines an abnormality in the number of respirations per unit time measured, and generates a corresponding output signal, based on which the object detecting section 40 is activated to prepare for monitoring the bed or thereabouts and again detects the target object when returned to the bed, thus reactuating the ROI setting section 10.

Figure 2:
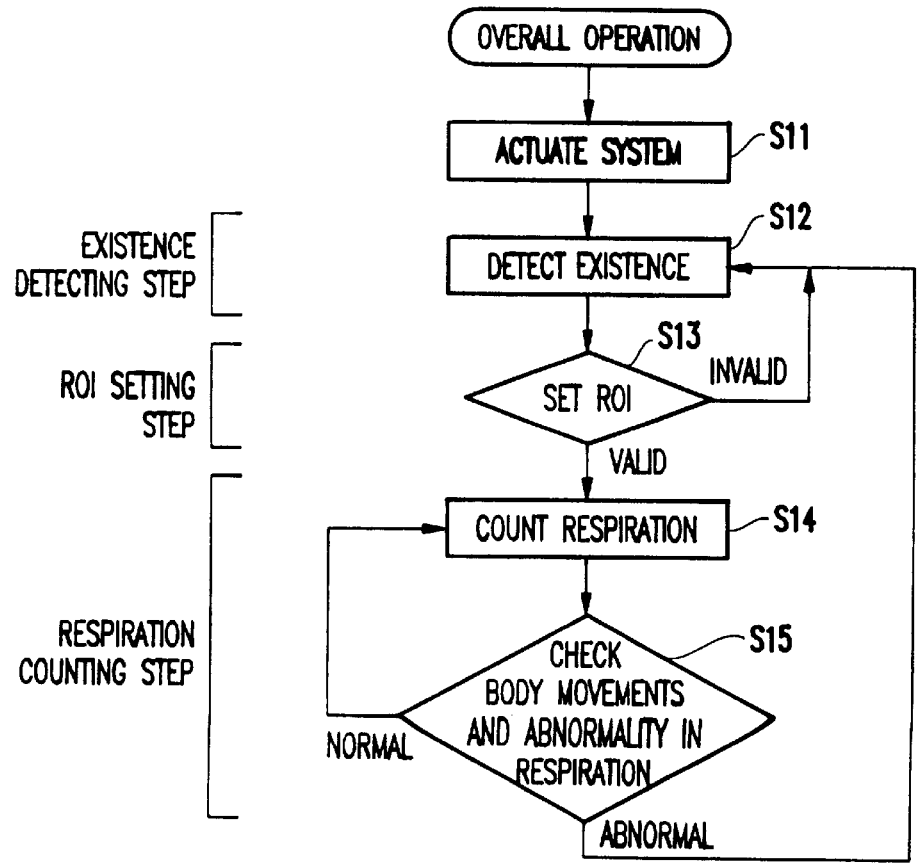
FIG. 2 is a flow chart showing the overall operation of the respiration monitoring system.

FIG. 2 is a flow chart illustrating the overall operation of the respiration monitoring system according to this embodiment.

Next, the overall operation of the respiration monitoring system will be described while referring to FIG. 2.

First, in step S11, the system is actuated, and in step S12, the object detecting section 40 starts to detect the presence and absence of a target object, i.e., whether a target object exists on a bed or thereabouts. Upon detection of the target object, the ROI setting section 10 sets a region of interest (ROI) in step S13. Upon setting of the ROI, the ROI setting section 10 sets a candidate for the ROI and determines validity or feasibility thereof. If it is determined that the setting of the ROI candidate is invalid, the control process or flow returns to the existence detecting step S12, and the above operations in steps S12 and S13 are repeatedly carried out until the ROI candidate thus obtained becomes valid.

If the ROI candidate setting is determined to be valid in step S13, the flow then goes to step S14 where respiration counting is carried out. Subsequently, in step S15, if it is determined that the number of respirations per unit time or the movement of the target object (e.g., body movement of a person to be monitored) is abnormal, there may be the possibility that the target object be away from the bed, and thus, the control process returns to the existence detecting step S12, whereas if the determination in step S15 is otherwise (i.e., abnormal), an alarm is generated by the abnormality determining section 30.

Figure 3:
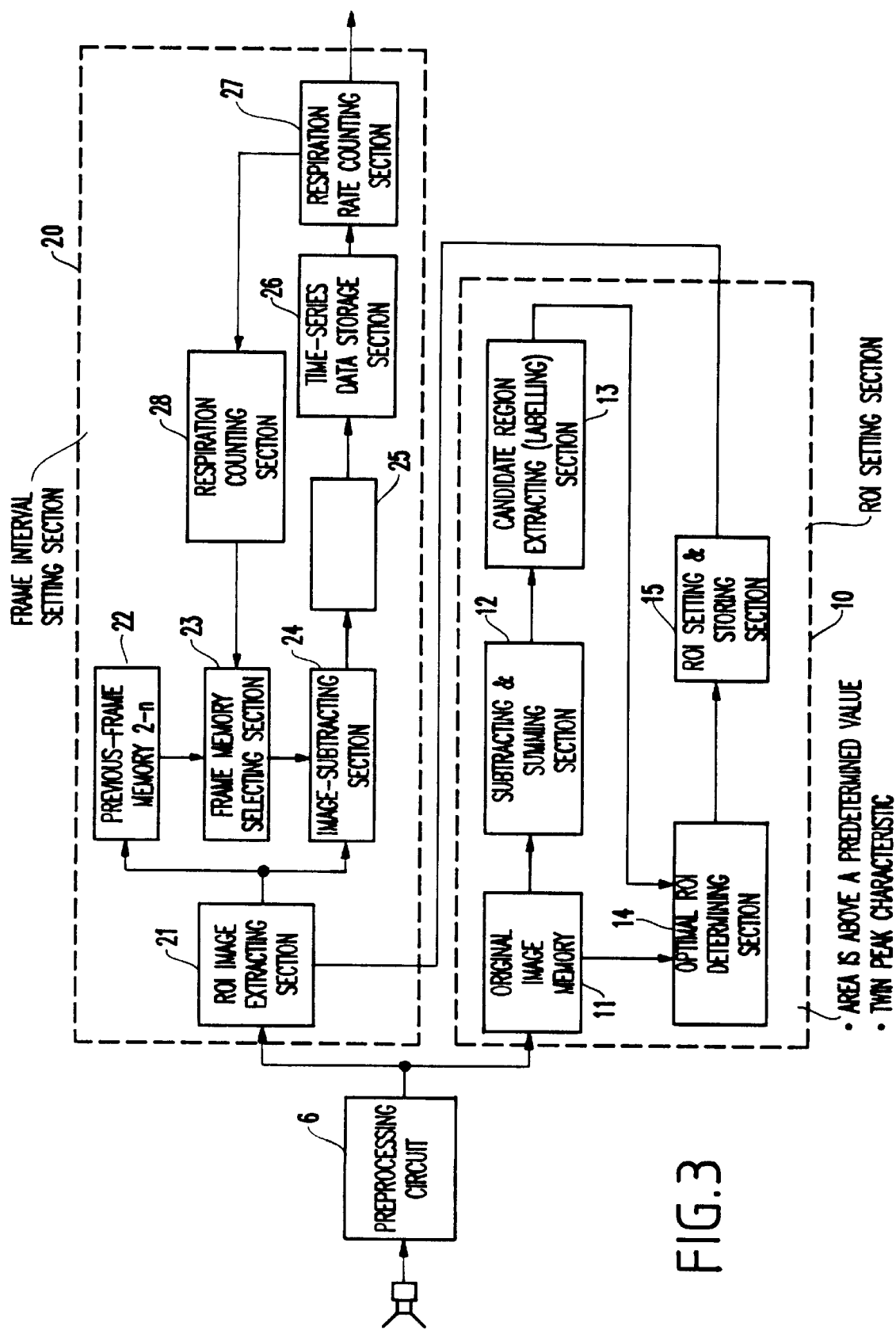
FIG. 3 is a block diagram showing the details of an ROI setting section and a respiration measuring section of this embodiment.

FIG. 3 shows in block form the details of the ROI setting section 10 and the respiration counting section 20 of the respiration monitoring system.

The ROI setting section 10 comprises an original image memory 11 connected to an output of a preprocessing circuit 6 that performs waveform shaping and the like, for continuously taking in the image obtained by the CCD camera 2 for a period of time equal to just half the respiration period, a subtracting and summing circuit 12 connected to an output of the original image memory 11 for extracting a changed portion of the image stored therein, a candidate-region extracting section 13 connected to an output of the subtracting and summing circuit 12 for labeling the summed image obtained by the subtracting and summing circuit 12 to provide a candidate region for the ROI, an optimal-ROI determining section 14 connected to an output of the candidate-region extracting section 13 and the output of the original image memory 11 for determining whether the region (imaginary region) extracted by the candidate-region extracting section 13 can be used as the ROI, and an ROI setting and storing section 15 connected to an output of the optimal-ROI determining section 14 for setting as the ROI the imaginary region that is determined to be appropriate or optimal for the ROI by means of the optimal-ROI determining section 14.

Here, it is to be noted that an unillustrated operation controller is connected to an output of the object detecting section 40 shown in FIG. 1.

The respiration counting section 20 comprises an ROI image extracting section 21 connected to the output of the preprocessing circuit 6 and the output of the ROI setting and storing section 15 for extracting from the image data obtained by the CCD camera 2 only those image data which lie within the ROI, a previous-frame memory 22 connected to an output of the ROI image extracting section 21 for storing ROI image data for n frame images, an interimage subtraction section 24 connected to an output of the ROI image extracting section 21 and an output of a frame memory selecting section 23 to be described later for performing subtraction between images spaced from each other a distance of $\alpha$ frames, and a surface integration section 25 connected to an output of the inter-image subtraction section 24 for surface integrating the values of the inter-image subtractions obtained thereby.

The respiration counting section 20 comprises a time-series-data storing section 26 connected to an output of the surface integration section 25 for storing, as time series data, the values of surface integration obtained by surface integrating the inter-image subtraction in a time serial manner for a predetermined period of time, a respiration rate calculating section 27 for calculating the number of respirations per unit time based on the data stored in the time-series-data storing section 26, a frame interval setting section 28 connected to an output of the respiration rate calculating section 27 for setting a frame interval $\alpha$ with which the inter-image subtraction section 24 performs inter-image subtraction, based on the result of calculation by means of the respiration rate calculating section 27, and the frame memory selecting section 23 connected to an output of the frame interval setting section 28 for selecting from the previous-frame memory 22 a previous frame image spaced an interval of $\alpha$ from a current image and outputting it to the inter-image subtraction section 24.

Figure 4:
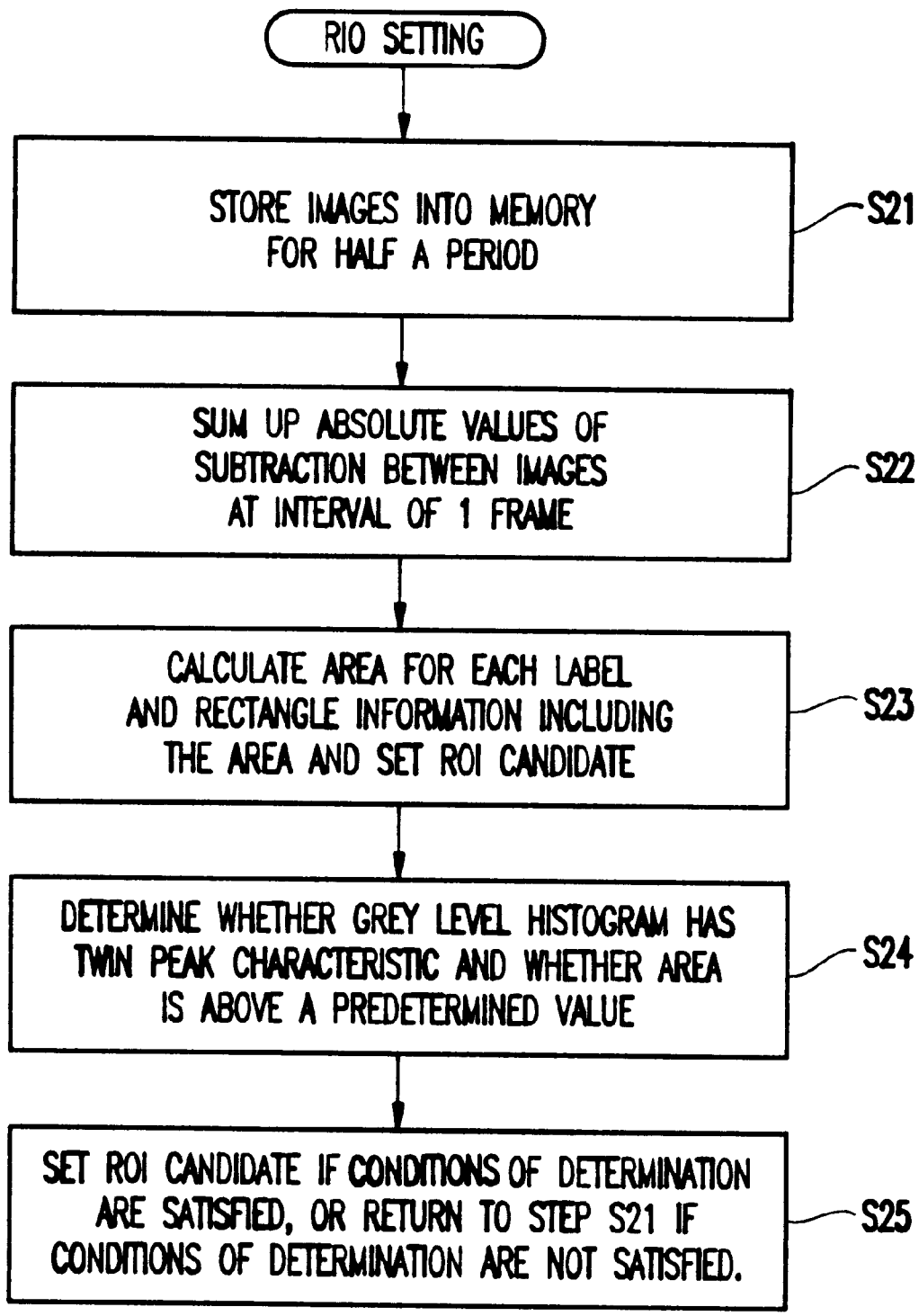
FIG. 4 is a flow chart showing the operation of the ROI setting section of this embodiment.

FIG. 4 is a flow chart illustrating the operation of the ROI setting section 10.

Now, the operation of ROI setting section 10 will be described while referring to the flow chart of FIG. 4.

Figure 5:
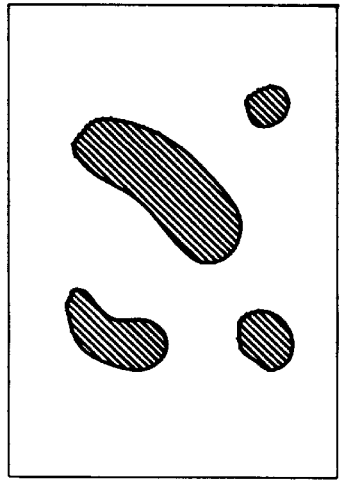
FIG. 5 is a view showing image change information obtained by a subtracting and summing circuit of this embodiment.

First, in step S21, images from the CCD camera 2 are stored into the original image memory 11 for a period of time equal to half the respiration period. In step S22, the subtracting and summing circuit 12 performs subtraction at a predetermined subtraction interval (e.g., one frame), and sums up information of changes which are given by absolute values of subtractions. An example of such information of changes thus summed up are shown in FIG. 5, wherein a plurality of dark portions indicate image portions for which changes have been recognized during a time equal to half the respiration period. In step S23, the candidate-region extracting section 13 carries out labeling processing on the information of image changes depicted in FIG. 5, and calculates an area and information of a rectangle enclosing the area for each label, thereby setting an ROI candidate.

Although in this embodiment, a plurality of ROI candidates with labels having gradually decreasing areas from the largest to smallest have been prepared, a single candidate having a label of the largest area can instead be used, and if it is determined according to an optimal-ROI determination to be described later that this candidate is not optimal, the control process returns to step S21 so as to set a new ROI candidate once again.

Figure 6:
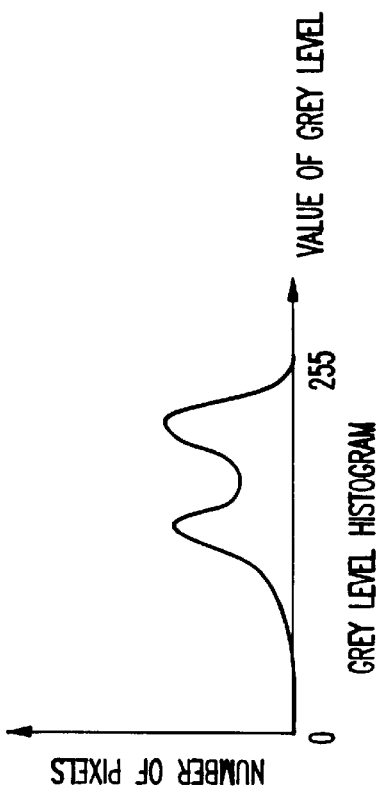
FIG. 6 is a gray level histogram.

In step S24, the optimal-ROI determining section 14 determines an optimal ROI. Specifically, in this optimal ROI determination, an original image date related to the position and size of a rectangular region information set in the first candidate is obtained from the original image memory 11, thus providing a gray level histogram indicative of distribution of the number of pixels at each gray level. The values of gray levels are determined according to 255 steps or degrees of gradation. An example of such a gray level histogram is shown in FIG. 6. In the gray level histogram, it is determined whether a twin peak characteristic including two adjacent peaks at a short interval can be recognized and whether the area of the region (i.e., rectangular region) listed as a candidate is equal to or greater than a predetermined value. If these conditions are not satisfied, the second candidate is taken as the next candidate for its optimality determination according to this embodiment, as referred to above.

Subsequently, if the conditions of determination are satisfied in step S24, the position and size or rectangular area of the optimal ROI are stored into the ROI setting and storing section 15, and thus the optimal ROI is finally set in step S25. On the other hand, if the conditions of determination are not satisfied, then the control process returns to step S21, thus repeating the optimal ROI setting processing.

After the optimal ROI has been set as described above, the respiration counting section 20 measures or counts the number of respirations per unit time using the ROI thus set.

Figure 7:
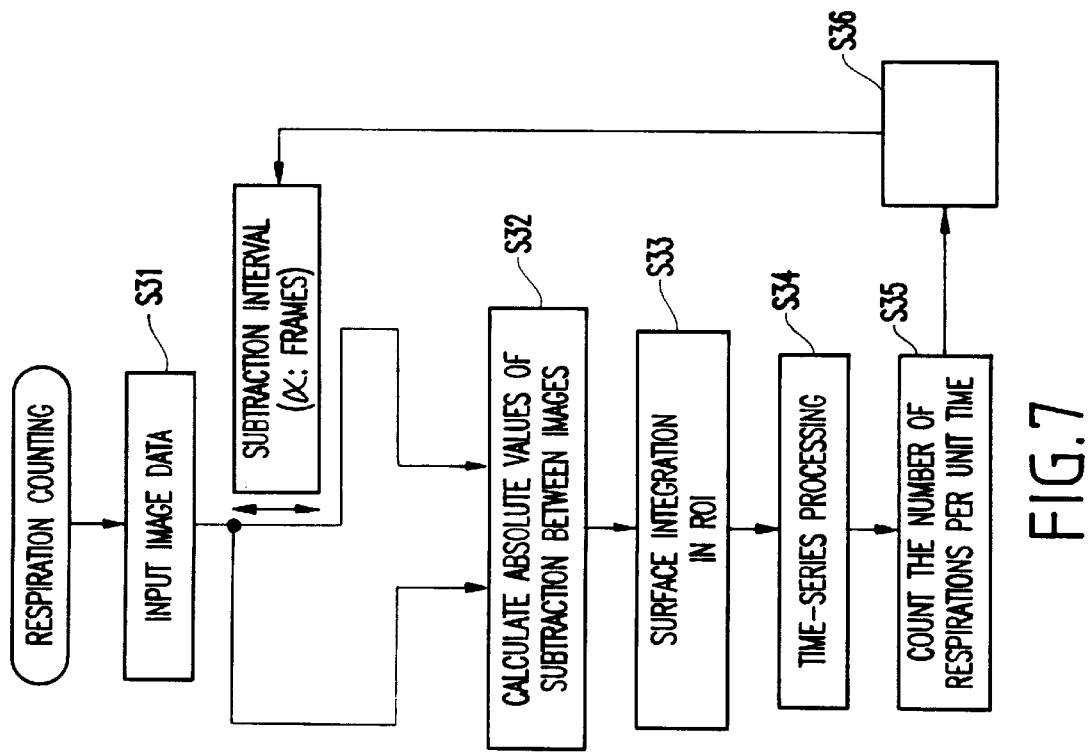
FIG. 7 is a flow chart showing respiration counting.

FIG. 7 is a flow chart illustrating the operation of the respiration counting section 20.

Next, the operation of the respiration counting section 20 will be described in detail while referring to the flow chart of FIG. 7.

First, in step S31, image data within the thus set ROI is input from the CCD camera 2 to the previous-frame memory 22 and stored therein. Subsequently, in step S32, the inter-image subtraction section 24 performs inter-image subtraction so as to provide an absolute value of subtraction for each pixel, which is then surface integrated by the surface integration section 25 in step S33

The above processes are carried out in a time-series manner, as shown in step S34, and the data obtained during such processes are stored in the time-series-data storing section 26, based on which data the respiration counting section 20 measures or counts the number of respirations per unit time in step S35.

FIG. 8 illustrates in real time the time-series data obtained by the surface integrating section 25. In this figure, the speed or rate of respiration is shown by the absolute value of subtraction, and as will be described in detail later, there clearly appear a plurality of high twin peaks each having a pair of peaks indicative of exhalation and inhalation, thus emphasizing changes or variations in spite of influences of noise thereon.

Here, the number of respirations per unit time is measured by counting the number of peaks exceeding a constant or fixed threshold $S_H$.

In step S36, the frame-interval setting section 28 automatically sets a frame interval in the form of the interval of subtraction $\alpha$ based on the number of respirations per unit time as measured in such a manner as to emphasize changes or variations in the value of surface integration (gray level), and outputs it to the frame memory selecting section 23 which then selects, based on the subtraction interval $\alpha$, a frame memory having a frame image stored therein previously apart an interval of a frames from the current image, and outputs the data therein to the inter-image subtraction section 24.

Here, it is to be noted that for the subtraction interval $\alpha$, a frame interval corresponding to half the respiration period for example is selected in order to maximally emphasize changes in the gray level or darkness. In view of this, the number of frames to be stored in the previous-frame memory 22 is suitably selected based on the number of frames per unit time and the respiration period. The previous-frame memory 22, in which the data used for inter-image subtraction was stored, now becomes available for storing the next image data. In cases where the frame interval $\alpha$ is set based on the respiration period (the number of respirations per unit time), as stated above, a change in the surface integration obtained may be multiplied by $1/\alpha$ in order to indicate the surface integration change at the same rate.

Embodiment 2

In the aforementioned embodiment 1, the respiration counting section 20 performs respiration counting using the ROI set by the ROI setting section 10, but in this case, the ROI setting section 10 may be constructed such that it is always preparing for setting a new ROI during respiration counting by the respiration counting section 20. In this case, as shown in FIG. 9, an optimal-ROI determining section 14A is provided with a temporal storage section 14a for storing an ROI each time the ROI is determined to be optimal by means of the optimal-ROI determining section 14A. Thus, for example, if the abnormality determining section 30 determines the presence of abnormality, the ROI setting section 10 can immediately reset the optimal ROI stored in the temporal storage section 14a in place of the current ROI set in the ROI setting and storing section 15. In this manner, it is possible to avoid interrupting respiration counting for the time required to reset a new ROI, thereby enabling respiration counting to re-start immediately. If it is again determined that the number of respirations per unit time freshly counted is abnormal, the abnormal respiration is immediately judged to be not due to inappropriate setting of the ROI, thus enabling speedy recovery treatments to be taken.

Embodiment 3

Although in the aforementioned embodiment 1, the respiration rate calculating section 27 counts the number of peaks using the constant or fixed threshold $S_H$, as shown in FIG. 8, the threshold $S_H$ may be varied for each peak. FIG. 10 shows in block form an exemplary arrangement of a respiration rate calculating section 27A in this case. The respiration rate calculating section 27A comprises a differential circuit 27a and a hold circuit 27b both connected to an output of a time-series data storing section 26 (see FIG. 3), a subtracter 27c connected to outputs of the hold circuit 27b and the time-series data storing section 26, a setter 27e in which a predetermined value is set, a comparator 27d connected to outputs of the subtracter 27c and the setter 27c, and a counter 27f connected to an output of the comparator 27d.

With the above arrangement, the differential circuit 27a differentiates the time-series data stored in the time-series data storing section 26 to find its peak, which is then output to the hold circuit 27b and held therein as a peak value. The subtracter 27c calculates a difference or subtraction between the peak value and the following time-series data, and outputs the thus calculated value of difference or subtraction to the comparator 27d in which the difference or subtraction value is compared with the set value in the setter 27e. The comparator 27d generates an output to the counter 27f when the subtraction value is greater than the set value. The counter 27f counts the number of outputs from the comparator 27d, thereby providing a count of peaks.

According to the respiration rate calculating section 27A, if a peak value varies, the threshold therein is accordingly changed to detect such a varying peak, so that the number of peaks can be counted accurately irrespective of the magnitude of each peak.

Embodiment 4

Moreover, in the above-mentioned embodiment 1, the abnormality determining section 30 is constructed such that it makes an abnormality determination based solely on the number of respirations per unit time as counted by the respiration rate calculating section 27. However, there may sometimes be the case where the abnormality determining section 30 can not measure the true respiration (i.e., respiratory movements) correctly, since the ROI once properly set is placed out of its original or intended position due to movements of an object to be monitored such as a patient or the like, or since the influence of noise affects respiration counting. In view of this, in order to determine whether respiration is counted correctly, a frequency spectrum of the time-series data can be obtained for comparison with a frequency spectrum of a normally or correctly measured respiration. In this case, such a comparison can be made using a statistical test of hypothesis.

Figure 11:
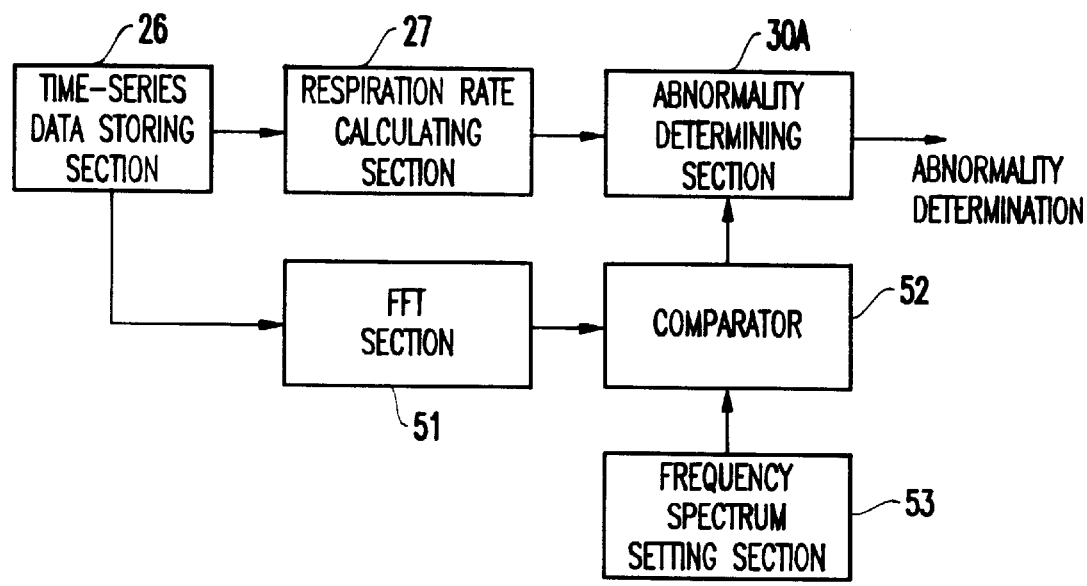
FIG. 11 is a block diagram showing an example for performing a frequency analysis of a time-series data in a respiration monitoring system in accordance with a fourth embodiment of the present invention.
Figure 12:
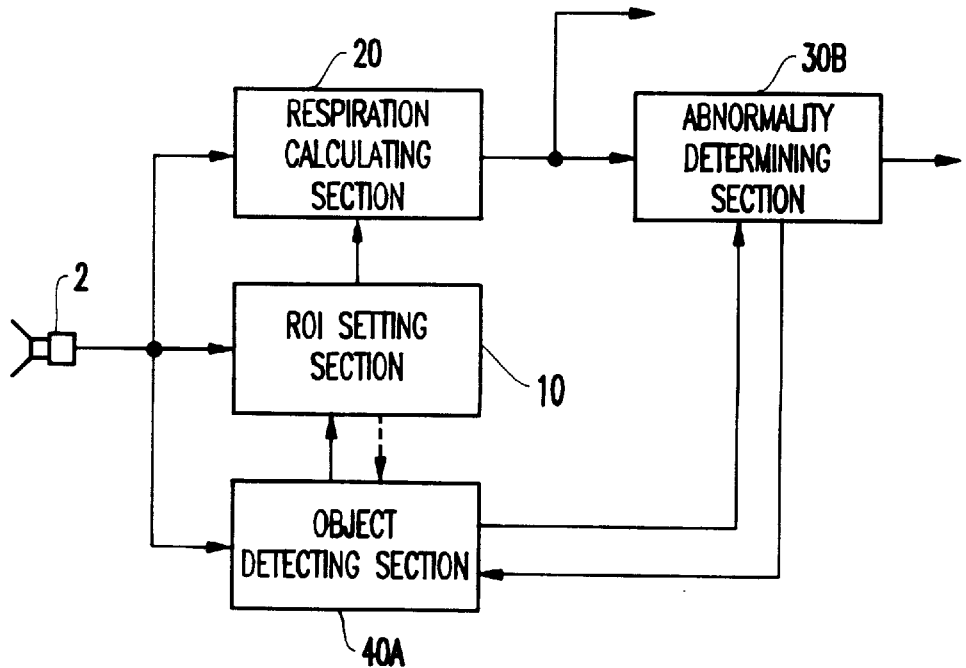
FIG. 12 is a block diagram showing the overall arrangement of a respiration monitoring system in accordance with a fifth embodiment of the present invention.
Figure 13:
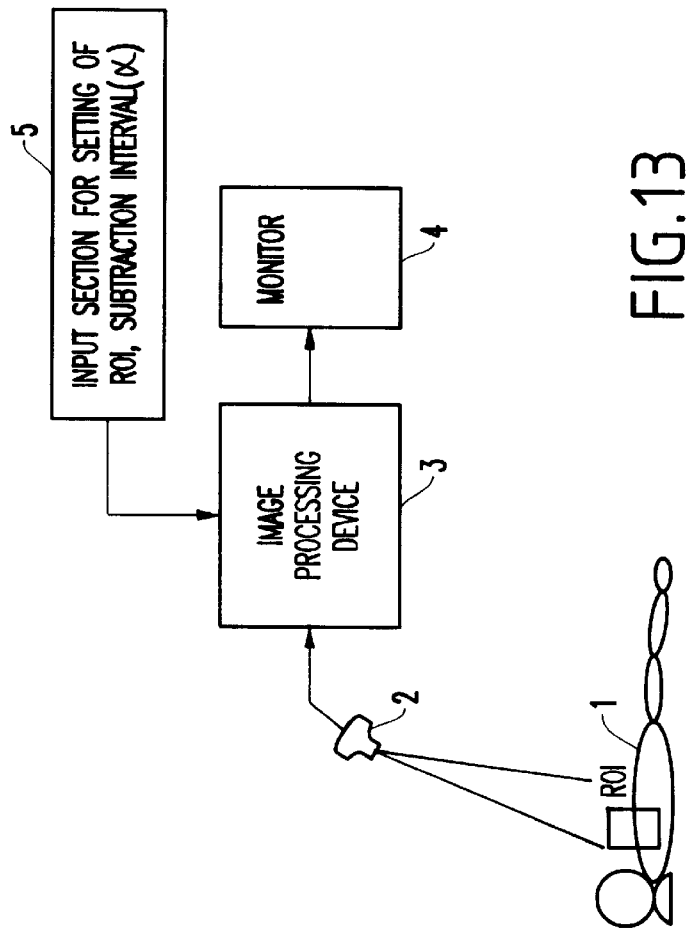
FIG. 13 is a block diagram showing a conventional respiration monitoring system.
Figure 14:
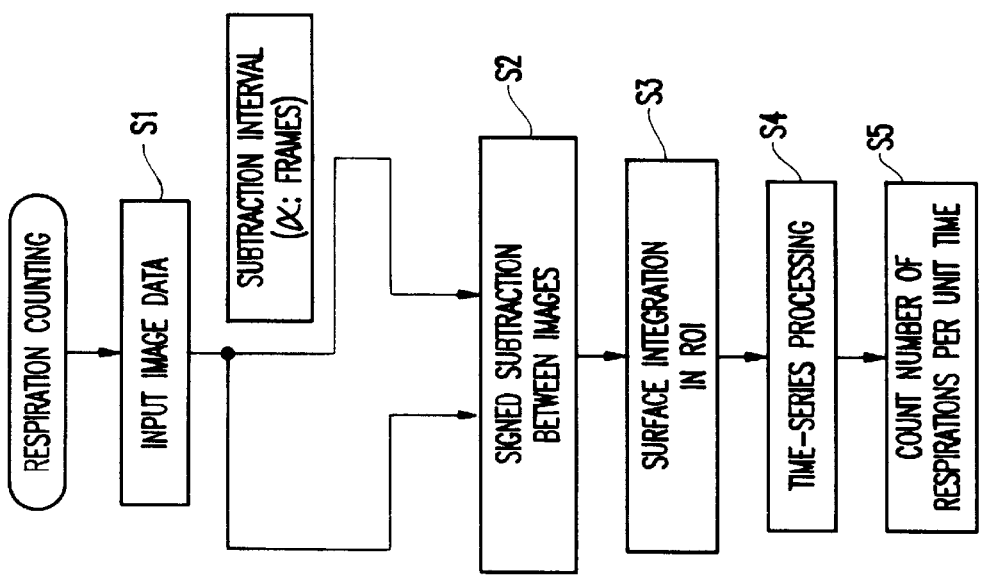
FIG. 14 is a flow chart showing the operation of the conventional respiration monitoring system.

FIG. 11 shows in block form an example of such an arrangement. In this figure, a fast Fourier transform (FFT) section 51 is provided at an output side of the time-series data storing section 26 for generating a frequency spectrum of the time-series data output therefrom. A comparator 52 compares the frequency spectrum of the time-series data output from the FFT section 51 with a normal or correct frequency spectrum set in a frequency spectrum setting section 53. This comparison is made, for example, in the terms of the magnitude or strength of a predetermined frequency component. An abnormality determining section 30A determines, based on the comparison result of the comparator 52, whether the respiration counting is normal.

Embodiment 5

Although in the aforementioned embodiment 1, the object detecting section 40 detects an object coming into the picture or the field of view of the CCD camera 2 upon setting an ROI, by detecting a large change in time of the images taken by the CCD camera 2, it may also detect the object going out of the picture or the field of view of the CCD camera 2 by detecting a large change in time of the images. A large change in time of the images can be detected, for example, by detecting a change in contrast or brightness of the images at predetermined time intervals by way of sensing correlation between the images or a change in the gray level histogram thereof. In this case, an object detecting section 40A according to this embodiment may be provided with an image memory for the above purpose, but instead the original image memory 11 of the ROI setting section 10 can be used for investigating correlation between the images, or gray level histograms can be compared with each other at a predetermined time interval using a statistical test of hypothesis so as to perform the above detection. When it is detected that the object to be monitored has gone out of the picture, the result of such a detection can be sent to an abnormality determining section 30B, so that it is possible to deal with the abnormal condition while discriminating respiratory abnormality from such an abnormal situation in which normal respiration counting can not be effected due to the absence of an object to be watched in the picture or the field of view of the CCD camera 2.

As described in detail in the foregoing, according to the present invention, automatic setting of the ROI can provide the advantage that there are obtained an ROI setting apparatus for respiration monitoring and a respiration monitoring system in which accurate automatic respiration counting can be effected for an extended period of time without requiring any watch man while maintaining a high degree of respiration counting accuracy. In addition, exhalation and inhalation of a person to be monitored can be recognized on a monitor in quite an easy manner.

While the invention has been described in terms of its preferred embodiments, it should be understood that numerous modifications may be made thereto without departing from the spirit and scope of the invention as defined in the appended claims. It is therefore intended that all such modifications fall within the scope of the claims.

What is claimed is:

1. A region-of-interest setting apparatus for respiration monitoring comprising:

photographing means for photographing an object to be monitored;

provisional-region setting means for extracting changed portions between successive images photographed by said photographing means and setting an optimal one of the thus extracted changed portions as a provisional region;

determining means for determining whether said provisional region set by said provisional-region setting means can be adopted as a changed region for respiration counting; and region-of-interest setting means for setting said provisional region as a region of interest for respiration counting when said determining means determines that said provisional region can be adopted as a changed region for respiration counting.

2. A region-of-interest setting apparatus for respiration monitoring according to claim 1, wherein said determining means determines whether in said provisional region set by said provisional-region setting means, a gray level histogram indicative of distribution of the number of pixels for respective gray level values includes a twin peak characteristic having twin peaks each equal to or higher than a predetermined value.

3. A region-of-interest setting apparatus for respiration monitoring, comprising:

photographing means for photographing an object to be monitored;

provisional-region setting means for extracting changed portions between successive images photographed by said photographing means and setting an optimal one of the thus extracted changed portions as a provisional region;

determining means for determining whether said provisional region set by said provisional-region setting means can be adopted as a changed region for respiration counting; and region-of-interest setting means for setting said provisional region as a region of interest for respiration counting when said determining means determines that said provisional region can be adopted as a changed region for respiration counting, wherein said provisional-region setting means comprises subtracted-image storing means for calculating absolute values of subtractions between every successive two of a plurality of frame images taken during at least half a respiration period, and for summing up and storing the absolute values of subtractions of the images thus obtained for every predetermined number of frames; and region-of-interest candidate setting means for calculating the position and size of each of said changed regions based on brightness information of each subtracted image stored in said subtracted-image storing means and setting at least the greatest among the changed regions as a provisional region.

4. A region-of-interest setting apparatus for respiration monitoring according to claim 3, wherein said determining means determines whether in said provisional region set by said provisional-region setting means, a gray level histogram indicative of distribution of the number of pixels for respective gray level values includes a twin peak characteristic having twin peaks each equal to or higher than a predetermined value.

5. A region-of-interest setting apparatus for respiration monitoring according to claim 4, wherein said determining means determines whether the area of said changed region is equal to or greater than a predetermined value.

6. A region-of-interest setting apparatus for respiration monitoring, comprising:

photographing means for photographing an object to be monitored;

provisional-region setting means for extracting changed portions between successive images photographed by said photographing means and setting an optimal one of the thus extracted changed portions as a provisional region;

determining means for determining whether said provisional region set by said provisional-region setting means can be adopted as a changed region for respiration counting; and region-of-interest setting means for setting said provisional region as a region of interest for respiration counting when said determining means determines that said provisional region can be adopted as a changed region for respiration counting, wherein said provisional-region setting means comprises subtracted-image storing means for calculating absolute values of subtractions between every successive two of a plurality of frame images taken during at least half a respiration period, and for summing up and storing the absolute values of subtractions of the images thus obtained for every predetermined number of frames; and region-of-interest candidate setting means for calculating the position and size of each of said changed regions based on brightness information of each subtracted image stored in said subtracted-image storing means and setting an optimal one of the changed regions successively from the greatest to the smallest thereof as a provisional region.

7. A region-of-interest setting apparatus for respiration monitoring according to claim 6, wherein said determining means determines whether in said provisional region set by said provisional-region setting means, a gray level histogram indicative of distribution of the number of pixels for respective gray level values includes a twin peak characteristic having twin peaks each equal to or higher than a predetermined value.

8. A region-of-interest setting apparatus for respiration monitoring according to claim 7, wherein said determining means determines whether the area of said changed region is equal to or greater than a predetermined value.

9. A region-of-interest setting apparatus for respiration monitoring, comprising:

photographing means for photographing an object to be monitored;

provisional-region setting means for extracting changed portions between successive images photographed by said photographing means and setting an optimal one of the thus extracted changed portions as a provisional region;

determining means for determining whether said provisional region set by said provisional-region setting means can be adopted as a changed region for respiration counting; and region-of-interest setting means for setting said provisional region as a region of interest for respiration counting when said determining means determines that said provisional region can be adopted as a changed region for respiration counting, wherein said determining means determines whether in said provisional region set by said provisional-region setting means, a gray level histogram indicative of distribution of the number of pixels for respective gray level values includes a twin peak characteristic having twin peaks each equal to or higher than a predetermined value, and wherein said determining means determines whether the area of said changed region is equal to or greater than a predetermined value.

10. A region-of-interest setting apparatus for respiration monitoring, comprising:

photographing means for photographing an object to be monitored;

provisional-region setting means for extracting changed portions between successive images photographed by said photographing means and setting an optimal one of the thus extracted changed portions as a provisional region;

determining means for determining whether said provisional region set by said provisional-region setting means can be adopted as a changed region for respiration counting; and region-of-interest setting means for setting said provisional region as a region of interest for respiration counting when said determining means determines that said provisional region can be adopted as a changed region for respiration counting, wherein when said determining means determines that said provisional region set by said provisional-region setting means can not be adopted as a changed region for respiration counting, said provisional region setting means again performs the setting of a provisional region.

11. A region-of-interest setting apparatus for respiration monitoring, comprising:

photographing means for photographing an object to be monitored;

provisional-region setting means for extracting changed portions between successive images photographed by said photographing means and setting an optimal one of the thus extracted changed portions as a provisional region;

determining means for determining whether said provisional region set by said provisional-region setting means can be adopted as a changed region for respiration counting; and region-of-interest setting means for setting said provisional region as a region of interest for respiration counting when said determining means determines that said provisional region can be adopted as a changed region for respiration counting; and region-of-interest setting starting-condition determining means for detecting, as a condition for starting the setting of a region of interest, whether the object to be monitored has come into a field of view of said photographing means.

12. A respiration monitoring system comprising:

photographing means for photographing an object to be monitored;

setting means for setting a region of interest for respiration counting in images taken by said photographing means;

change detecting means for calculating absolute values of subtractions between successive two images taken by said photographing means in the region of interest set by said setting means and for summing up the absolute values of subtractions for every predetermined number of frames; and counting means for counting the number of respirations per unit time based on a trend of time-series changes obtained by said change detecting means.

13. A respiration monitoring system, comprising:

photographing means for photographing an object to be monitored;

setting means for setting a region of interest for respiration counting in images taken by said photographing means;

change detecting means for calculating absolute values of subtractions between successive two images taken by said photographing means in the region of interest set by said setting means and for summing up the absolute values of subtractions for every predetermined number of frames;

counting means for counting the number of respirations per unit time based on a trend of time-series changes obtained by said change detecting means; and condition determining means for determining, based on a frequency analysis of a trend of time-series data, whether the state of respiration is normal.

14. A respiration monitoring system according to claim 13, further comprising existence determining means for determining whether the object to be monitored has gone out of a predetermined range of photographing.

15. A respiration monitoring system according to claim 14, wherein said respiration counting means counts the number of respirations per unit time by measuring the number of peaks in a change of a trend in the time series data, and wherein a threshold is used which is set for each peak for counting thereof.

16. A respiration monitoring system, comprising:

photographing means for photographing an object to be monitored;

setting means for setting a region of interest for respiration counting in images taken by said photographing means;

change detecting means for calculating absolute values of subtractions between successive two images taken by said photographing means in the region of interest set by said setting means and for summing up the absolute values of subtractions for every predetermined number of frames;

counting means for counting the number of respirations per unit time based on a trend of time-series changes obtained by said change detecting means; and existence determining means for determining whether the object to be monitored has gone out of a predetermined range of photographing.

17. A respiration monitoring system, comprising:

photographing means for photographing an object to be monitored;

setting means for setting a region of interest for respiration counting in images taken by said photographing means;

change detecting means for calculating absolute values of subtractions between successive two images taken by said photographing means in the region of interest set by said setting means and for summing up the absolute values of subtractions for every predetermined number of frames; and counting means for counting the number of respirations per unit time based on a trend of time-series changes obtained by said change detecting means, wherein said respiration counting means counts the number of respirations per unit time by measuring the number of peaks in a change of a trend in the time series data, and wherein a threshold is used which is set for each peak for counting thereof.

18. A respiration monitoring system, comprising:

photographing means for photographing an object to be monitored;

setting means for setting a region of interest for respiration counting in images taken by said photographing means;

change detecting means for calculating absolute values of subtractions between successive two images taken by said photographing means in the region of interest set by said setting means and for summing up the absolute values of subtractions for every predetermined number of frames;

counting means for counting the number of respirations per unit time based on a trend of time-series changes obtained by said change detecting means, and frame-interval setting means for setting said predetermined number based on the summed value calculated by said change detecting means or the number of respirations per unit time counted by said counting means in such a manner as to emphasize changes in gray levels.

19. A respiration monitoring system comprising:

photographing means for photographing an object to be monitored;

setting means for setting a region of interest for respiration counting in images taken by said photographing means;

change detecting means for calculating absolute values of subtractions between successive two images taken by said photographing means in the region of interest set by said setting means and for summing up the absolute values of subtractions for every predetermined number of frames; and counting means for counting the number of respirations per unit time based on a trend of time-series changes obtained by said change detecting means, wherein said setting means comprises region-of-interest setting means for setting a provisional region as a region of interest for respiration counting when it is determined that said provisional region can be adopted as a changed region for respiration counting.

20. A respiration monitoring system according to claim 19, wherein at least one of said provisional region setting means and said determining means operates during respiration counting.

* * * * *